United States Patent [19]

Ohsawa et al.

[11] Patent Number: 5,424,647
[45] Date of Patent: Jun. 13, 1995

[54] COMBUSTION DETECTION DEVICE FOR INTERNAL COMBUSTION ENGINE PROVIDED WITH A VOLTAGE REGULATING CIRCUIT TO PREVENT PREMATURE COMBUSTION

[75] Inventors: Toshio Ohsawa; Shigemi Murata, both of Hyogo, Japan

[73] Assignee: Mitsubishi Denki Kabushiki Kaisha, Tokyo, Japan

[21] Appl. No.: 986,728

[22] Filed: Dec. 8, 1992

[30] Foreign Application Priority Data

Dec. 9, 1991 [JP] Japan .................. 3-324276

[51] Int. Cl.⁶ .................. F02P 17/00; F02P 3/04
[52] U.S. Cl. .................. 324/378; 73/35; 324/399
[58] Field of Search .......... 324/378, 380, 388, 391, 324/393, 399; 73/35 I, 116

[56] References Cited

U.S. PATENT DOCUMENTS

| | | |
|---|---|---|
| 4,653,460 | 3/1987 | Ooyabu et al. |
| 4,762,106 | 8/1988 | Blaubut . |
| 5,067,462 | 11/1991 | Iwata et al. . |
| 5,087,882 | 2/1992 | Iwata .................. 324/388 |
| 5,143,042 | 9/1992 | Scheid .................. 324/399 X |
| 5,180,984 | 1/1993 | Murata et al. .................. 324/399 |
| 5,189,373 | 2/1993 | Murata et al. .................. 324/388 X |

FOREIGN PATENT DOCUMENTS

| | | |
|---|---|---|
| 3934310 | 4/1990 | Germany . |
| 4133015 | 4/1992 | Germany . |
| 56-96159 | 8/1981 | Japan . |

Primary Examiner—Gerard R. Strecker
Attorney, Agent, or Firm—Sughrue, Mion, Zinn, Macpeak & Seas

[57] ABSTRACT

A combustion detect device for use in an internal combustion engine including an ignition coil in which a high voltage for ignition is generated at a secondary winding when the current of a primary winding is cut off, and an ignition plug for discharging and igniting a mixture gas when said high voltage for ignition is applied thereto, the combustion detect device comprises an ion current detection device for detecting an ion current generated due to combustion of a mixture gas by applying a voltage to an ignition plug and a restriction device for restricting a voltage generated in the secondary winding when a primary winding is turned on to conduct.

6 Claims, 11 Drawing Sheets

COMBUSTION DETECTION DEVICE FOR INTERNAL COMBUSTION ENGINE PROVIDED WITH A VOLTAGE REGULATING CIRCUIT TO PREVENT PREMATURE COMBUSTION

BACKGROUND OF THE INVENTION

1. Field of the Invention

The present invention relates to a combustion detection device for use in an internal combustion engine.

2. Description of the Conventional Art

Figure 24:
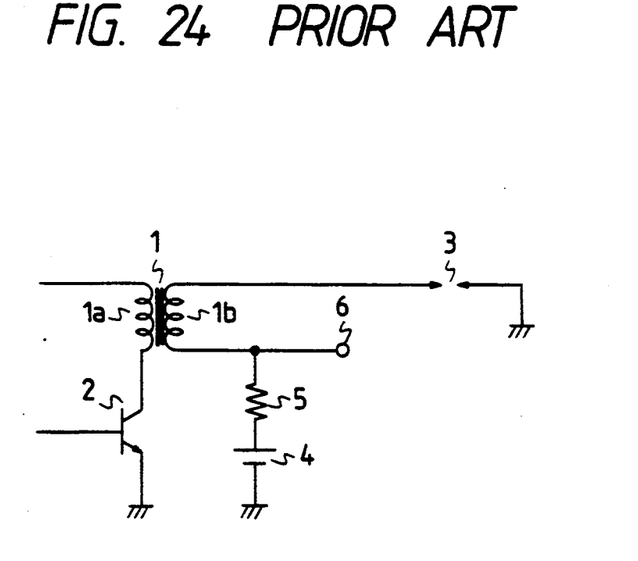
FIG. 24 is a circuit diagram of a conventional combustion detect device.

Description will be given below of an example of a conventional combustion detect device of this type with reference to FIG. 24. In FIG. 24, reference numeral 1 designates an ignition coil which includes a primary winding 1a and a secondary winding 1b; 2, a power transistor which is connected to the primary winding 1a and is used to cut off a primary current flowing through the primary winding 1a; 3, an ignition plug which is connected to the secondary winding 1b and, when a high voltage for ignition is applied thereto, is able to ignite a gas mixture of an internal combustion engine (not shown); 4, a power supply which is to apply a bias voltage of a positive polarity to the ignition plug 3 as bias means; 5, a resistor which is connected to the power supply 4 in series and is used to convert an ion current into a voltage; and 6, an output terminal which is used to detect the voltage across the resistor 5 and cooperates with the resistor 5 in forming ion current detect means.

In the above-mentioned structure, at the ignition timing of the internal combustion engine, the power transistor 2 is turned off to thereby cut off the primary current of the primary winding 1a, then there is produced an ignition high voltage of a negative polarity in the secondary winding 1b to thereby cause discharge across the electrode of the ignition plug 3, so that the gas mixture of the internal combustion engine can be ignited.

In this operation, with the combustion of the gas mixture, there is produced ionization, so that ions are generated. Here, the electrode of the ignition plug 3, after the abovementioned discharge, acts as an electrode for detecting an ion current and an ion current flows due to the movement of electrons caused by the bias of a positive polarity by the power supply 4. Therefore, by detecting a voltage across the resistor 5 due to the ion current at the output terminal 6, the combustion of the gas mixture can be confirmed.

However, in the above-mentioned conventional combustion detection device, when the power transistor 2 is turned on to thereby allow the primary winding 1a to conduct, there is generated a high voltage of 1-2 KV in the secondary winding 1b. For this reason, in the case of an ignition coil 1 of a plug-top type being used, the high voltage would cause the ignition plug 3 to discharge before its normal ignition time, so that a premature ignition can occur.

SUMMARY OF THE INVENTION

The present invention eliminates the above-mentioned drawbacks found in the conventional combustion detection device. Accordingly, it is an object of the invention to provide a combustion detection device for use in an internal combustion engine which prevents a premature ignition.

To attain the above object, according to the invention, there is provided a combustion detection device for use in an internal combustion engine, which comprises: an ion current detection device for detecting an ion current generated due to combustion of a gas mixture by applying a voltage to an ignition plug and a restriction device for restricting a voltage generated in the secondary winding when a primary winding is conductive.

According to the first aspect of the invention, the restriction means of the combustion detect device comprises a series circuit including a high tension diode and a resistor or a Zener diode respectively connected across a secondary winding.

Also, according to another aspect of the invention, the restriction means of the combustion detect device comprises a series circuit including a high tension diode and a Zener diode respectively, which is connected between one end of a secondary winding of an ignition coil and a coil power supply or ground.

Further, according to still another aspect of the invention, the restriction means of the combustion detect device comprises a parallel circuit including a high tension diode and a resistor or a Zener diode respectively connected between an ignition high voltage generation end of a secondary winding and an ignition plug, and another high tension diode connected between the other end of the secondary winding and the ignition plug.

According to the present invention, while a primary winding is conductive, there is generated in a second winding a voltage which is restricted by a restriction means.

DETAILED DESCRIPTION OF PREFERRED EMBODIMENTS

Now, description will be given hereinbelow of the embodiments of the invention with reference to the accompanying drawings.

Embodiment 1

Figure 1:
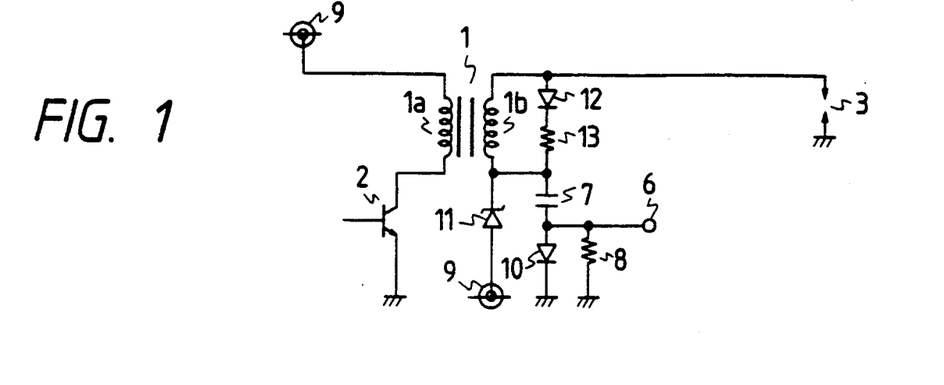
FIG. 1 is a circuit diagram of an embodiment 1 of a combustion detect device according to the invention.

FIG. 1 shows a circuit diagram of an embodiment 1 of a combustion detection device according to the invention, in which reference numeral 7 designates a capacitor which is connected to the positive side of a secondary winding 1b, and 8 refers to a resistor which is connected between the capacitor 7 and the ground and is used to convert an ion current into a voltage. The resistor 8 cooperates with an output terminal 6 in forming an ion current detect means. Reference numeral 10 designates a diode connected in parallel to the resistor 8, 11 refers to a Zener diode connected between the output end of the secondary winding 1b and a coil power supply 9, and 12, 13 point out a series connection of a high tension diode and a resistor, respectively, where the series connection is connected in parallel to the secondary winding 1b.

Figure 2A:
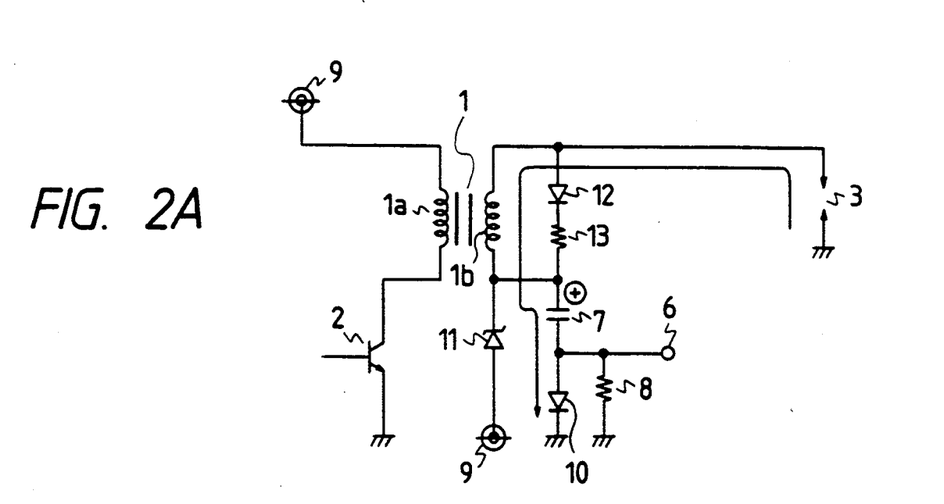
FIGS. 2A and 2B are explanatory views of an operation of the embodiment 1 according to the invention.

Next, description will be given of the operation of embodiment 1. While an ignition coil 1 is on, there is generated a given voltage from the series circuit composed of the high tension diode 12 and resistor 13 respectively connected to the secondary winding 1b, and the given voltage can be set arbitrarily according to the resistance value of the resistor 13. On the other hand, at an ignition time, the current of the primary winding 1a is cut off, and there is generated in the secondary winding 1b an ignition high voltage (of the order of −10 to −25 KV), and a discharge current is allowed to flow along a path shown by arrows in FIG. 2A to thereby ignite a gas mixture of an internal combustion engine. At that time, the capacitor 7 is charged by the discharge current to a polarity shown in FIG. 2A. It should be noted here that the charging voltage of the capacitor 7 can be set arbitrarily by the Zener diode 11.

Figure 2B:
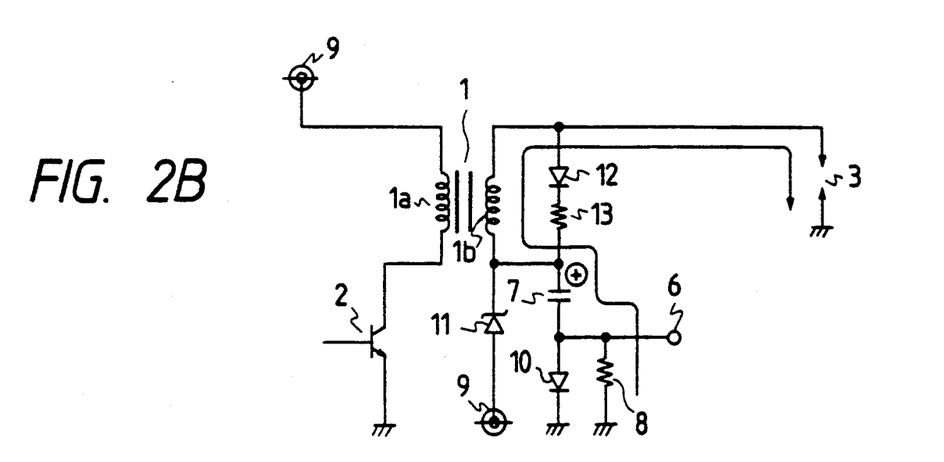

At the time of combustion of the gas mixture there is produced ionization to thereby generate ions similarly as in the prior art. At that time an ion current is allowed to flow in such a manner as shown by arrows in FIG. 2B due to the movement of electrons caused by the positive polarity bias (of the order of 50 to 300 V) of the capacitor 7. Therefore, combustion of the gas mixture can be confirmed by detecting a voltage which is generated in the output terminal 6 as a result of generation of the ion current. In this manner, according to embodiment 1, when a power transistor 2 is turned on to thereby allow the primary winding 1a to conduct, a voltage to be generated in the secondary winding 1b is regulated by the high tension diode 12 and resistor 13 respectively connected in series across the secondary winding 1b. That is, the voltage to be generated on the secondary winding can be controlled properly to thereby prevent premature ignition.

Embodiment 2

Figure 3:
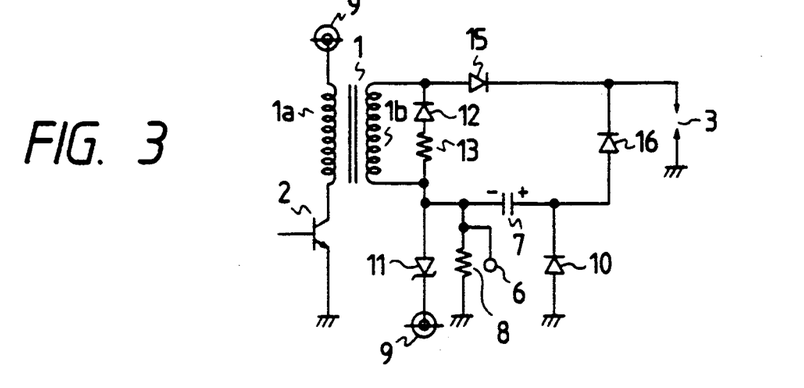
FIGS. 3 to 5 are circuit diagrams of embodiments 2 to 4 of the combustion detect device according to the invention.

In embodiment 1, description was given of a case in which the ignition coil 1 generates the ignition high voltage of a negative polarity. However, according to a second embodiment of the invention, the ignition coil 1 may be constructed in such a manner that it generates an ignition high voltage of a positive polarity, shown in FIG. 3. In FIG. 3, reference characters 15, 16 respectively designate diodes. In the second embodiment, the diode 10, Zener diode 11 and high tension diode 12 are oriented reversely to the embodiment 1 shown in FIG. 1. A discharge current flows along a path which includes a secondary winding 1b, a diode 15, an ignition plug 3, ground, a diode 10, a capacitor 7 and a secondary winding 1b and, in this case, the capacitor 7 is charged to a polarity shown in FIG. 3. Also, an ion current flows along a path which includes the capacitor 7, a diode 16, the ignition plug 3, the ground, a resistor 8 and the capacitor 7. The other portions of the structure and operation effects of the second embodiment are similar to those of the embodiment 1.

Embodiment 3

Figure 4:
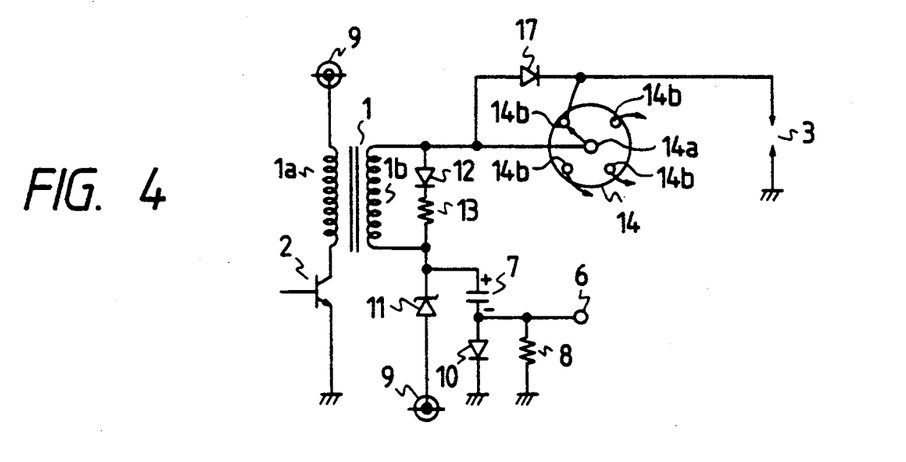

FIG. 4 shows a circuit diagram employed in a third embodiment of the invention. In this figure, reference numeral 14 designates a distributor which includes a central electrode 14a and a plurality of peripheral electrodes 14b, and 17 refers to a diode. And an ignition coil 1 is adapted to generate an ignition high voltage of a negative polarity. A discharge current flows along a path which includes a secondary winding 1b, a capacitor 7, a diode 10, ground, an ignition plug 3, peripheral electrodes 14b, an air gap, a central electrode 14a, and a secondary winding 1b. The other portions of the structure, operation and effects of the embodiment 3 are similar to those of the previously described embodiments 1 and 2.

Embodiment 4

Figure 5:
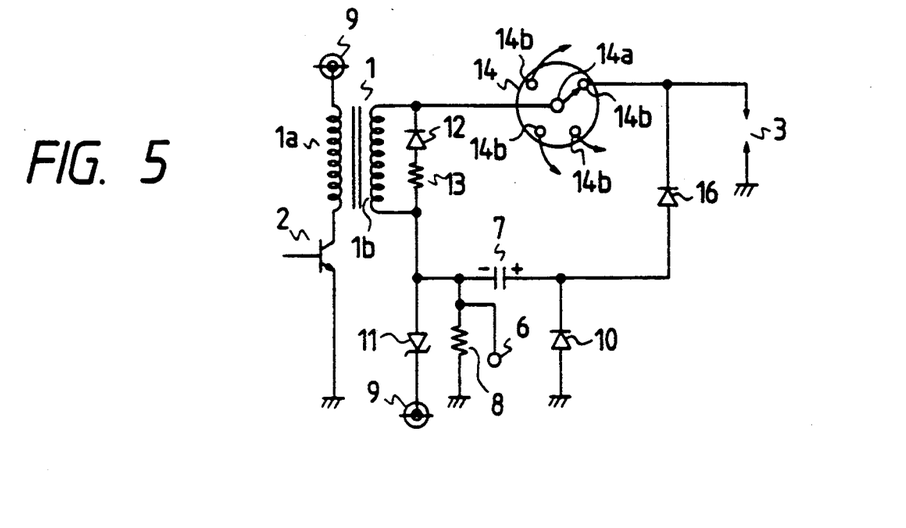

FIG. 5 shows a circuit diagram employed in a fourth embodiment of the invention. In this figure, reference numeral 14 designates a distributor which includes a central electrode 14a and a plurality of peripheral electrodes 14b, and 17 refers to a diode. An ignition coil 1 is adapted to generate an ignition high voltage of a positive polarity. A discharge current flows along a path which includes a secondary winding 1b, a central electrode 14a, an air gap, peripheral electrodes 14b, an ignition plug 3, ground, a diode 10, a capacitor 7 and a secondary winding 1b. The capacitor 7 is charged to a polarity shown in FIG. 5. Also, an ion current flows along a path which includes a capacitor 7, a diode 16, an ignition plug 3, ground, a resistor 8 and a capacitor 7. The other portions of the structure, operation and effects of the embodiment 4 are similar to those of the previously described embodiments 1, 2 and 3.

It should be noted here that, in embodiments 1 to 4, the ion current detect means is adapted to convert a voltage by the resistor 8. However, this is not limitative but other structures may be employed.

Embodiment 5

Figure 6:
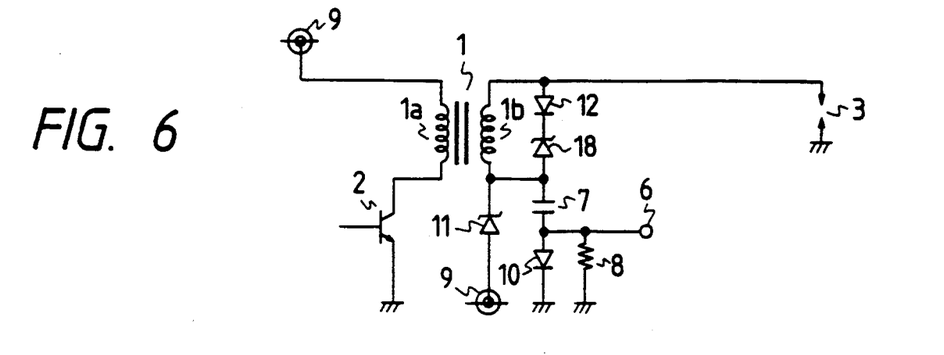
FIG. 6 is a circuit diagram of an embodiment 5 of a combustion detect device according to the invention.
Figure 7A:
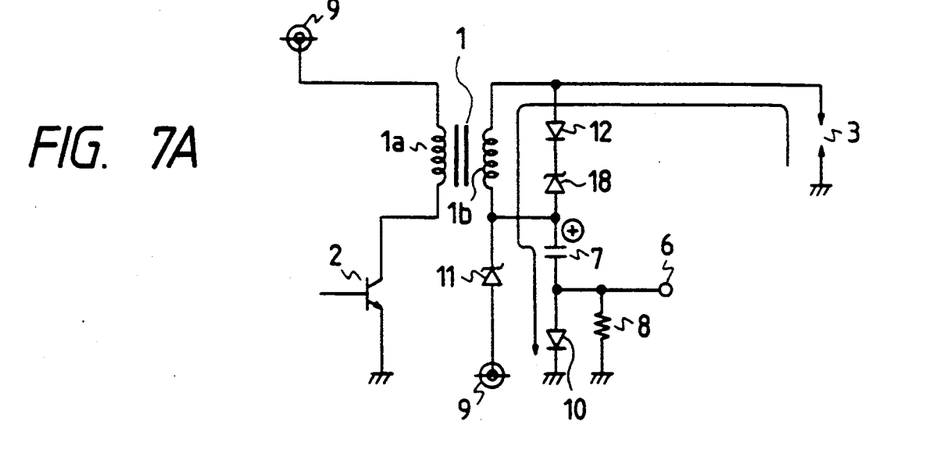
FIGS. 7A and 7B are explanatory views of an operation of the embodiment 5 according to the invention.
Figure 7B:
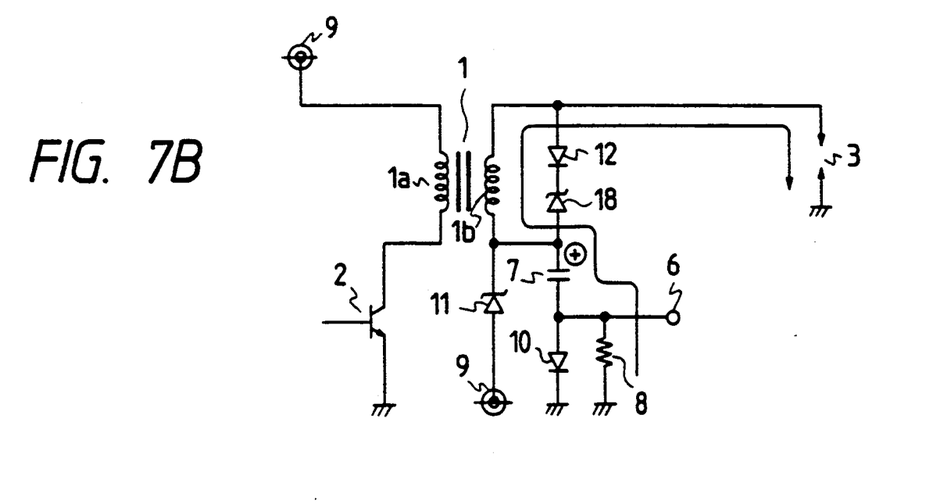

FIG. 6 shows a circuit diagram employed in a fifth embodiment of the invention. In FIG. 6, across a secondary winding 1b, there is connected a series circuit which is composed of a high tension diode 12 and a Zener diode 18, and other portions of the structure of the embodiment 5 are similar to those of embodiment 1 shown in FIG. 1. In the above-mentioned structure, when a primary winding 1a is allowed to conduct, there is generated a given voltage from the series circuit which is composed of the high tension diode 12 and Zener diode 18 respectively connected to the secondary winding 1b, and the given voltage can be set arbitrarily according to the Zener voltage value of the Zener diode 18. Also, at an ignition time, there is generated an ignition high voltage of a negative polarity (−10 to −25 KV) in the secondary winding 1b, and a discharge current is allowed to flow along a path shown by arrows in FIG. 7A to thereby cause discharge between the electrodes of the ignition plug 3, so that a gas mixture of an internal combustion engine can be ignited. At the same time, the capacitor 7 is charged by the discharge current, as a polarity shown in FIG. 7A. The charge voltage of the capacitor 7 can be set arbitrarily by the Zener diode 11. Also, an ion current flows in a manner as shown in FIG. 7B and, by detecting the ion current by means of the output terminal 6, combustion of the gas mixture can be confirmed. In embodiment 5, a voltage to be generated on the secondary side of the ignition coil 1 when it is conductive is controlled by the high tension diode 12 and Zener diode 18, thereby preventing premature ignition.

Embodiments 6 to 8

Figure 8:
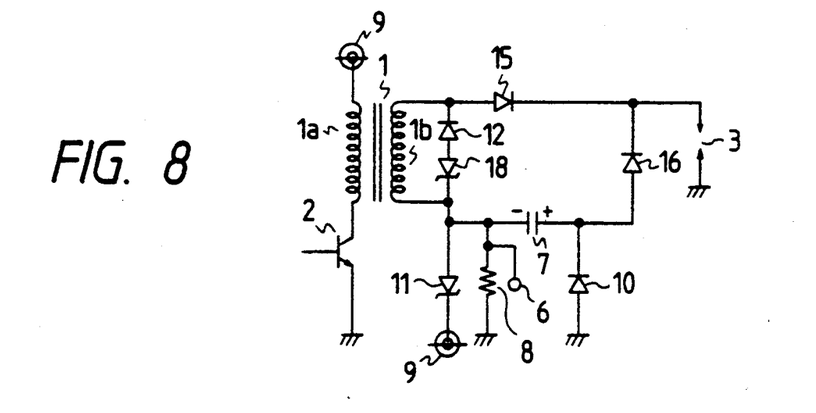
FIGS. 8 to 10 are circuit diagrams of embodiments 6 to 8 of the combustion detect device according to the invention.
Figure 9:
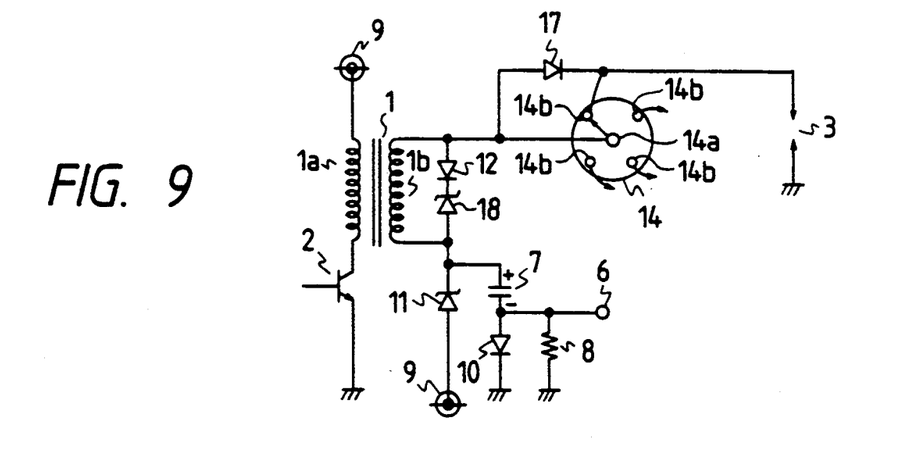
Figure 10:
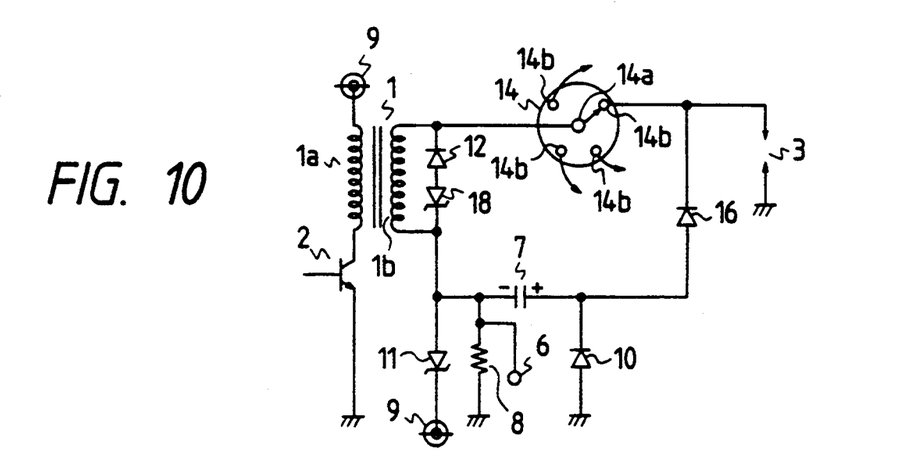

FIGS. 8 to 10 respectively show circuit diagrams which are respectively employed in embodiments 6 to 8 according to the invention. In each of these figures, there is provided a Zener diode 18 instead of the resistor 13 shown in FIGS. 3 to 5. The operation and effects of the embodiments 6 to 8 are similar to those of embodiments 2, 3 and 4.

Embodiment 9

Figure 11:
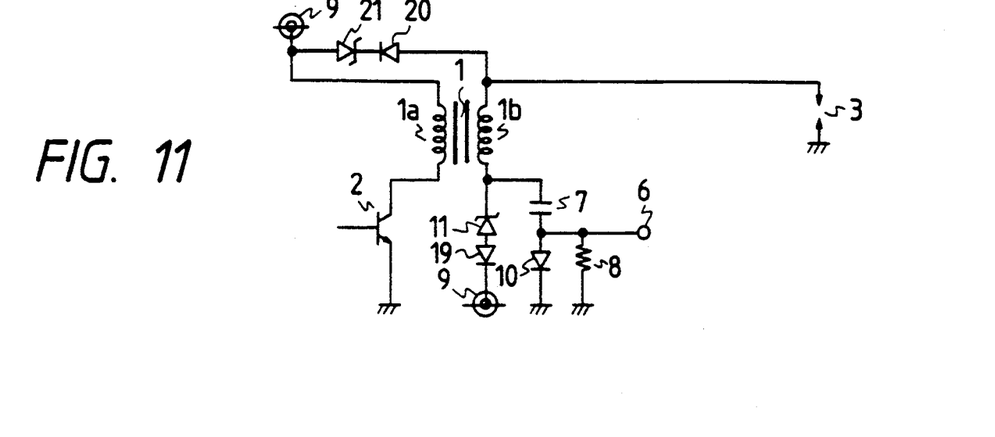
FIG. 11 is a circuit diagram of an embodiment 9 of a combustion detect device according to the invention.

FIG. 11 shows a circuit diagram employed in a ninth embodiment the invention. In FIG. 11, between an end opposite the coil ignition high voltage generation end of a secondary winding 1b and a coil power supply 9, there are provided a high tension diode 19 and a Zener diode 11 connected in series to each other. Also, between the coil ignition high voltage generation end of the secondary winding 1b and a coil power supply 9, there is provided a series circuit which is composed of a high tension diode 20 and a Zener diode 21. Other reference characters designate the same parts as in the previously described embodiments of the invention.

Figure 12A:
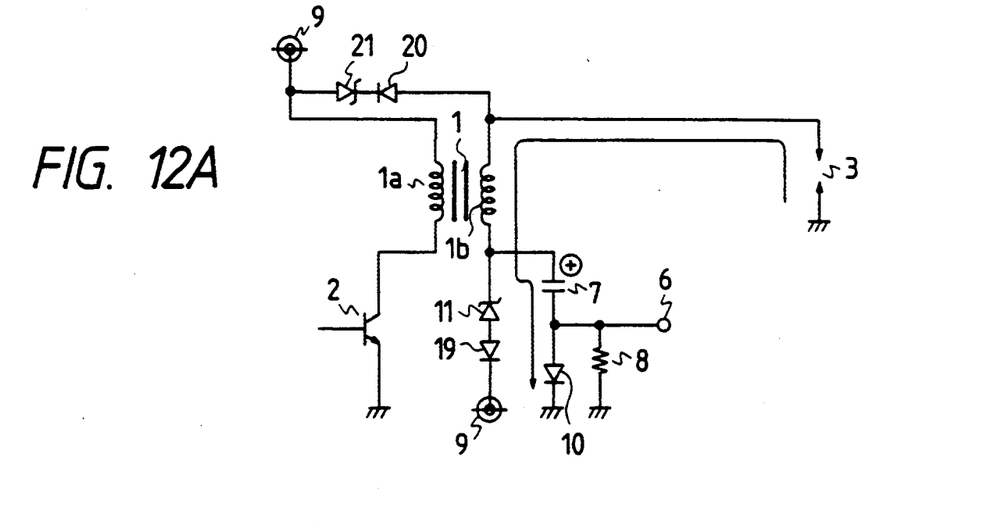
FIGS. 12A and 12B are explanatory views of an operation of the embodiment 9 according to the invention.
Figure 12B:
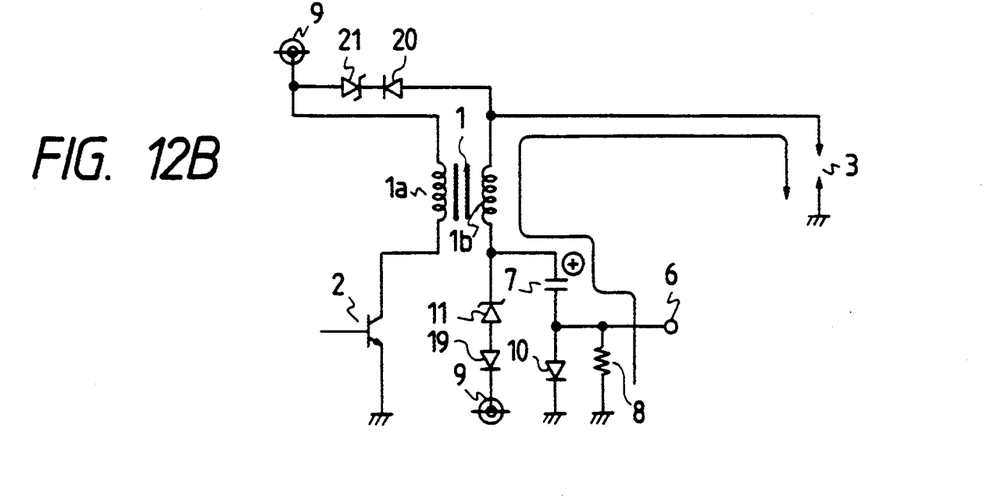

In the above-mentioned structure, when the ignition coil 1 is allowed to conduct, there is generated a given voltage in the secondary winding 1b by the high tension diode 20 and the Zener diode 21 and the given voltage can be set arbitrarily according to the Zener voltage values. Also, at an ignition time, there is generated an ignition high voltage of a negative polarity (on the order of −10 to −25 KV) in the second winding 1b, and a discharge current is allowed to flow in a path shown by arrows in FIG. 12A to thereby generate discharge between the electrodes of the ignition plug 3, so that the gas mixture of the internal combustion engine can be ignited. At the same time, the capacitor 7 is charged, while the charge voltage of the capacitor 7 can be set arbitrarily by the Zener diode 11. With combustion of the gas mixture, there is generated ionization which in turn causes ions to be generated, and an ion current is allowed to flow along a path shown by arrows in FIG. 12A by means of the positive polarity bias (on the order of 50 to 300 V) of the capacitor 7. By detecting the voltage across in the resistor 8 by means of the output terminal 6, combustion of the gas mixture can be confirmed. In embodiment 9, a high voltage to be generated on the secondary side when the ignition coil 1 is on is controlled in common by the series circuit composed of the high tension diode 19 and Zener diode 11 and by the series circuit composed of the high tension diode 20 and Zener diode 21 (alternatively, it may be controlled by one of the series circuits), thereby preventing premature ignition.

Embodiment 10

Figure 13:
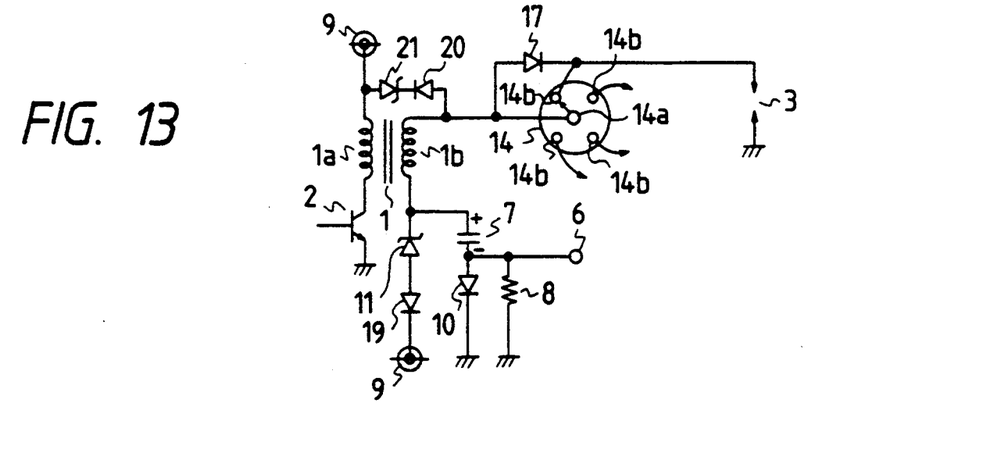
FIG. 13 is a circuit diagram of an embodiment 10 of a combustion detect device according to the invention.

FIG. 13 shows a circuit diagram which is employed in a tenth embodiment of the invention. In this embodiment, there is employed a high tension distribution system using a distributor 14 and a secondary winding 1b which is adapted to generate a high voltage for ignition. A discharge current is allowed to flow along a path which includes a secondary winding 1b, a capacitor 7, a diode 10, ground, an ignition plug 3, a plurality of peripheral electrodes 14b of the distributor 14, an air gap, a central electrode 14a of the distributor 14, and the secondary winding 1b. The effects of the embodiment 10 are similar to those of the embodiment 9.

Embodiment 11

Figure 14:
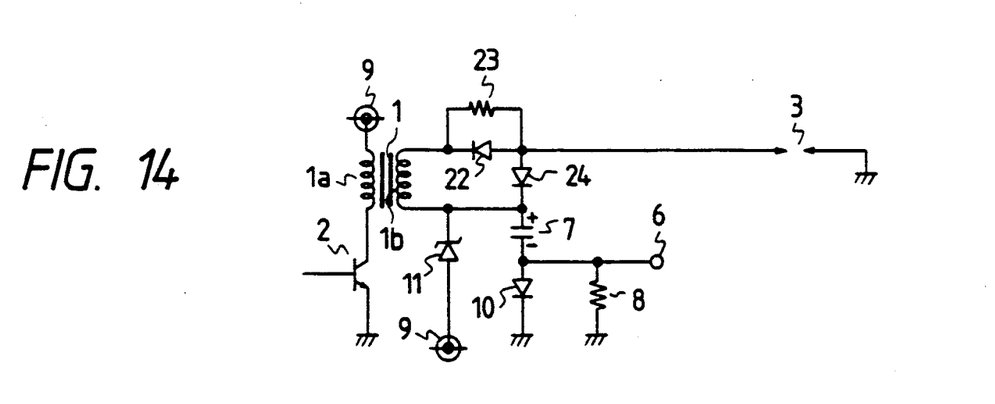
FIG. 14 is a circuit diagram of an embodiment 11 of a combustion detect device according to the invention.

FIG. 14 shows a circuit diagram which is employed in an eleventh embodiment of the invention. In this figure, reference numerals 23 and 24 respectively correspond to a resistor and a high tension diode which are connected in parallel between the ignition high voltage generation end of a secondary winding 1b and an ignition plug 3. The high tension diode is connected between the output terminal of the secondary winding 1b opposite to the ignition high voltage generation end thereof and the ignition plug 3. Other reference characters stand for the same parts as shown in the previously described embodiments.

Figure 15A:
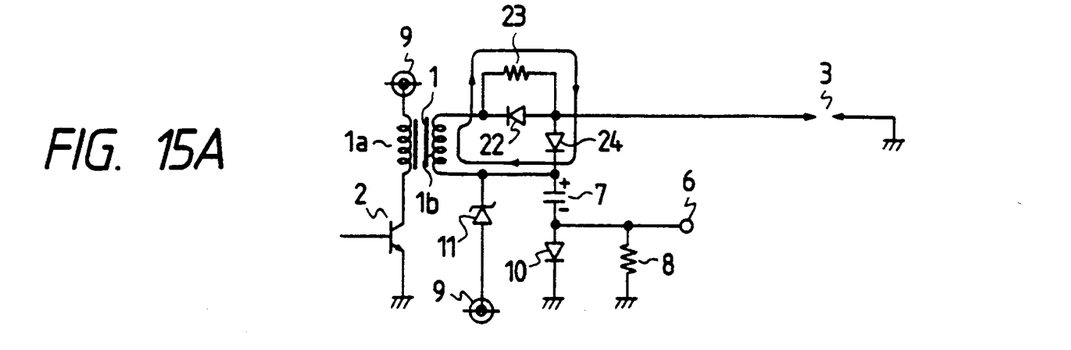
FIGS. 15A to 15C are explanatory views of an operation of the embodiment 11 according to the invention.
Figure 15B:
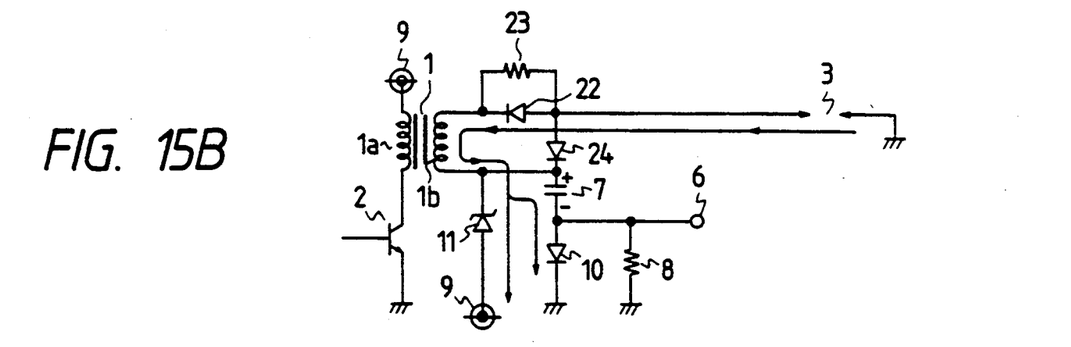

In the above-mentioned structure, when the ignition coil 1 is on, a current is allowed to flow in such a manner as shown by arrows in FIG. 15A, and voltages are caused to drop at the two ends of the resistor 23, whereby a voltage in the connecting portion of the resistor 23 and ignition plug 3 can be controlled. On the other hand, when the conduction of the primary winding 1a is gut off by the power transistor 2 at an ignition time, then there is generated in the secondary winding 1b an ignition high voltage of a negative polarity (on the order of −10 to −25 V), and a discharge current is allowed to flow along a path shown by arrows in FIG. 15B to thereby cause discharge between the electrodes of the ignition plug 3, so that the mixture gas of the internal combustion engine can be ignited and at the same time the capacitor 7 is charged to a polarity shown. The charging voltage can be set arbitrarily by the Zener diode 11.

Figure 15C:
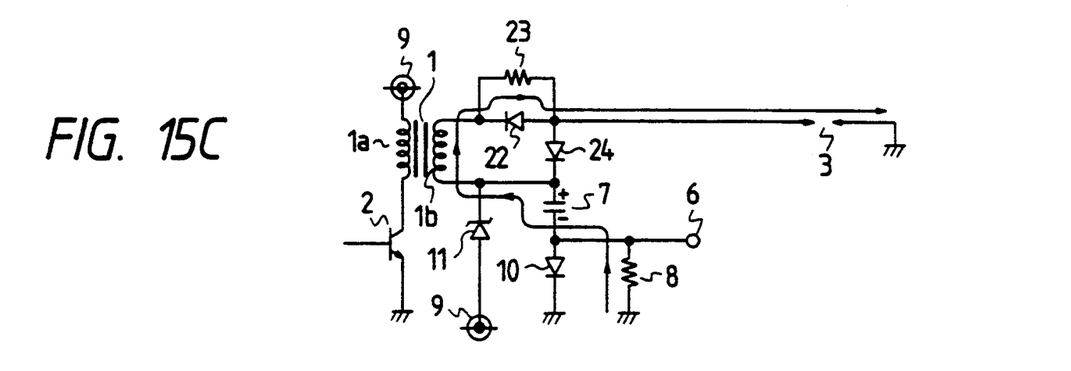

In this operation, with combustion of the gas mixture, there is generated ionization which in turn causes ions to be generated and an ion current is allowed to flow along a path shown by arrows in FIG. 15C due to the movement of electrons caused by the positive bias (on the order of 50 to 300 V) of the capacitor 7. At that time, by detecting a voltage, to be generated in the resistor 8 by means of the output terminal 6, combustion of the mixture can be confirmed.

Embodiments 12-14

Figure 16:
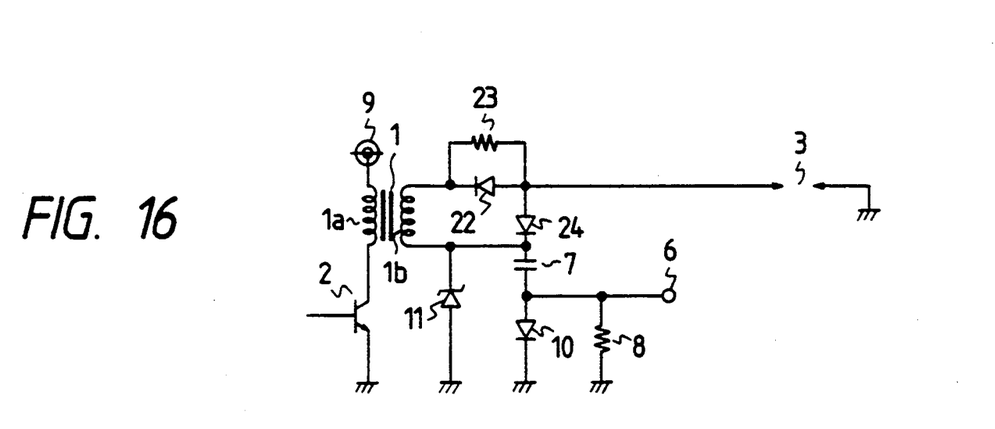
FIGS. 16 to 18 are circuit diagrams of embodiments 12 to 14 of the combustion detect device according to the invention.
Figure 17:
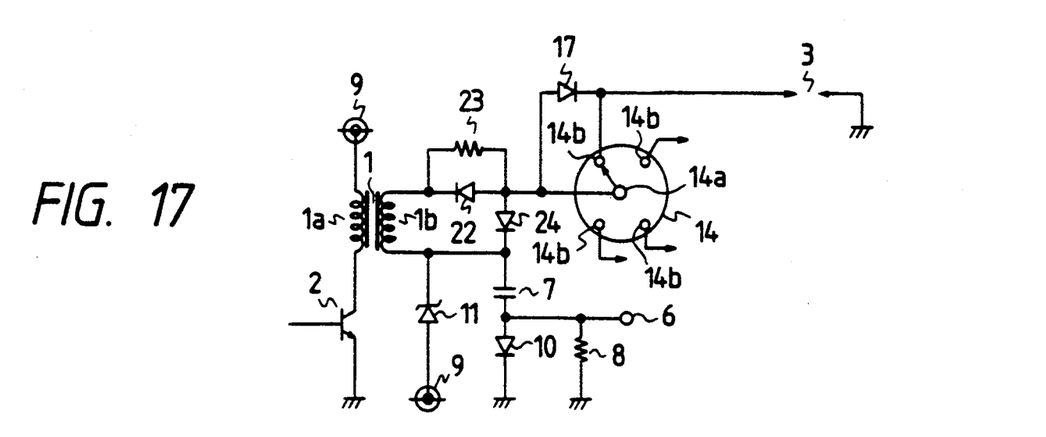
Figure 18:
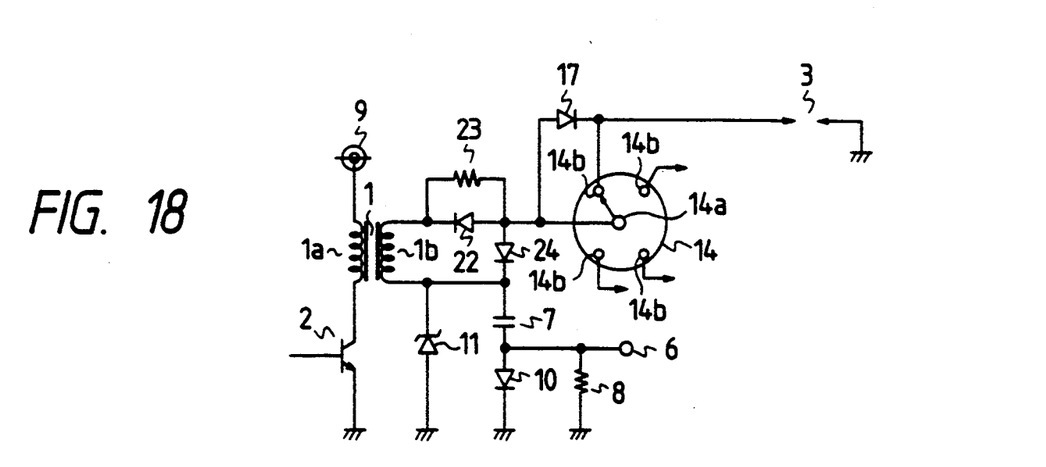

FIG. 16 shows a circuit diagram which is employed in a twelfth embodiment of the invention. In this embodiment, although one terminal of a Zener diode 11 is not connected to a coil power supply 9 but is grounded, there can be provided similar effects as in the previously described embodiments of the invention. Also, FIG. 17 shows a circuit diagram which is employed in an embodiment 13 according to the invention. In the embodiment 13, there is employed a high tension distribution system using a distributor 14, not an independent ignition system. In this case, a secondary winding 1b generates a high voltage of a negative polarity and a discharge current flows along a path which includes a secondary winding 1b, a capacitor 7, a diode 10, ground, an ignition plug 3, a distributor 14 (including peripheral electrodes 14b —air gap—central electrode 14a), and the secondary winding 1b. Other operation and effects of the embodiment 13 are similar to those of the previous embodiments of the invention. Further, FIG. 18 shows a circuit diagram which is employed in a fourteenth embodiment. In this embodiment, one terminal of the Zener diode 11 in FIG. 17 is grounded.

Embodiments 15–18

Figure 19:
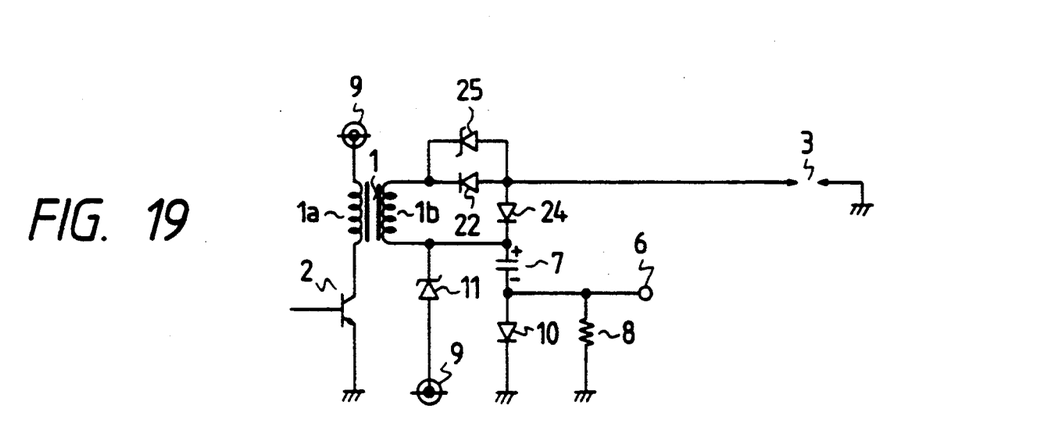
FIG. 19 is a circuit diagram of an embodiment 15 of a combustion detect device according to the invention.
Figure 20A:
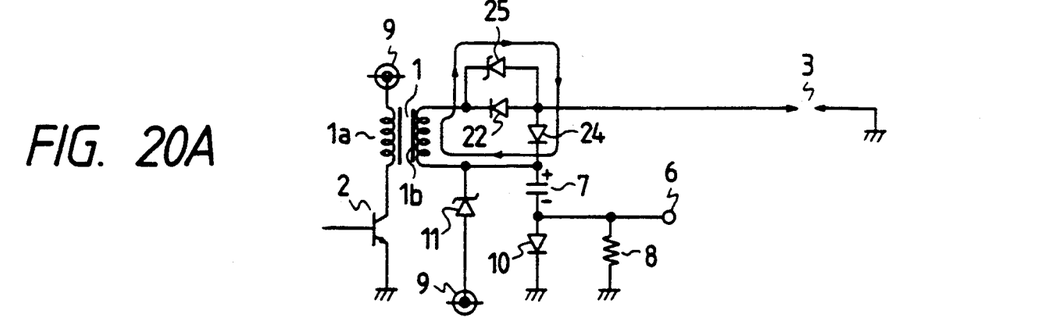
FIGS. 20A to 20C are explanatory views of an operation of the embodiment 15 according to the invention.
Figure 20B:
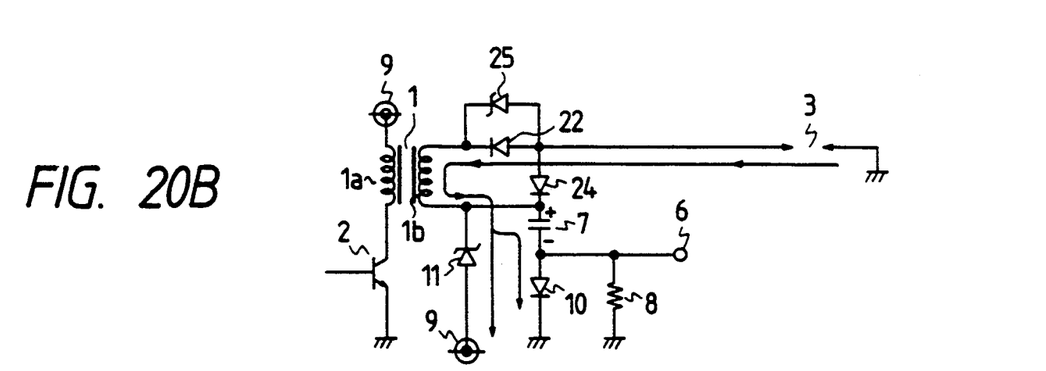
Figure 20C:
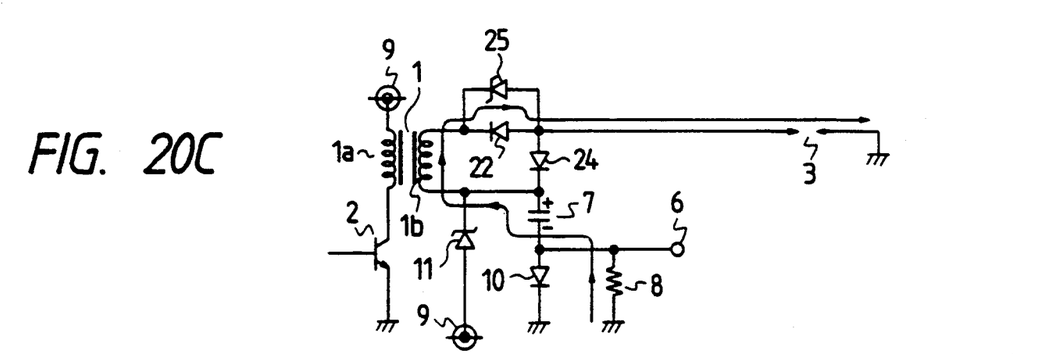
Figure 21:
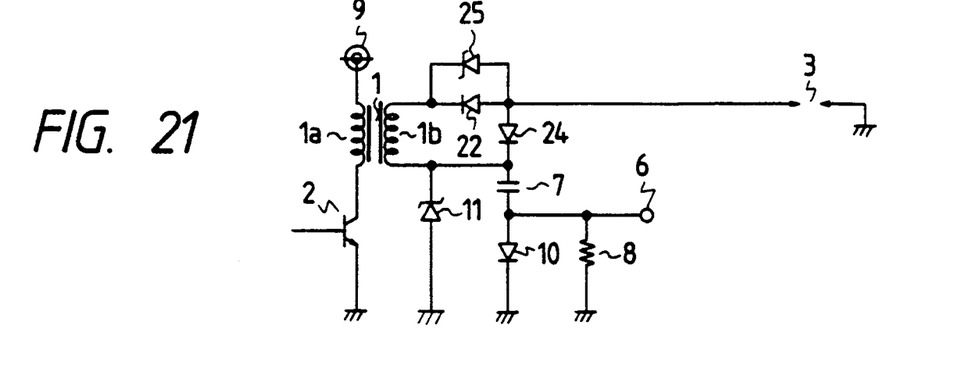
FIGS. 21 to 23 are circuit diagram of embodiments 16 to 18 of the combustion detect device according to the invention.
Figure 22:
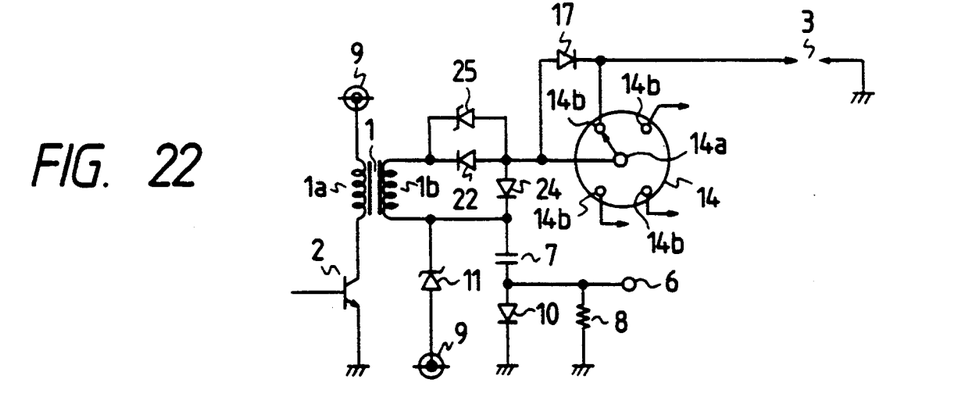
Figure 23:
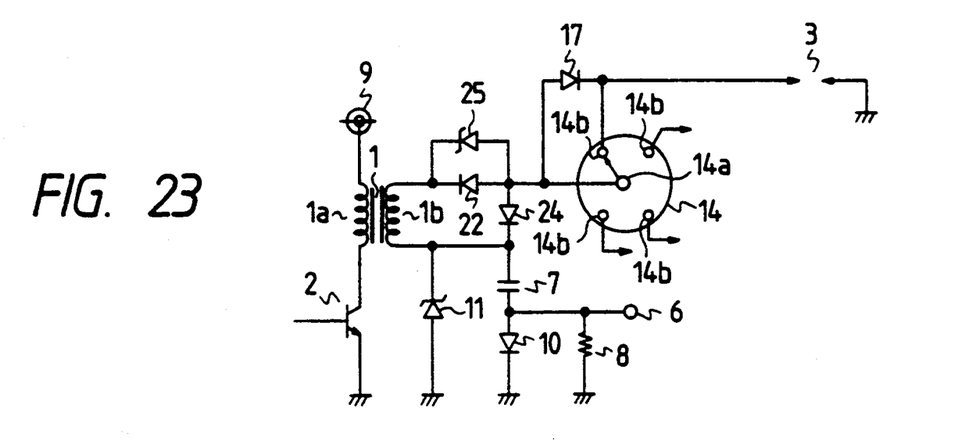

FIG. 19 shows a circuit diagram which is employed in a fifteenth embodiment of the invention. In this embodiment, there is provided a Zener diode 25 in place of the resistor 23 which is shown in FIG. 14. The operation of the embodiment 15, as shown in FIGS. 20A to 20C, is similar to that of the embodiment 11 shown in FIG. 14 and the effects thereof are also similar to those of the embodiment 11. Also, FIGS. 21 to 23 respectively show circuit diagrams which are employed in embodiments 16 to 18 according to the invention, respectively. In the respective embodiments 22 to 24, there is provided a Zener diode 25 in place of the resistor 23 shown in FIG. 14. The operation and effects of these embodiments are similar to those of the previously described embodiments of the invention.

As has been described heretofore, according to the invention, a voltage to be generated in a secondary winding when an ignition coil is on can be controlled and the voltage generated does not cause the ignition plug to discharge, thereby preventing premature ignition before a normal ignition time.

What is claimed is:

1. A combustion detection device for use in an internal combustion engine including an ignition coil, having a primary winding and a secondary winding, in which a high voltage for ignition is generated at an ignition high voltage generation end of said secondary winding when a current of said primary winding is cut off, and at least one ignition plug for discharging and igniting a gas mixture when said high voltage for ignition is applied to said at least one ignition plug, said combustion detection device comprising:
   ion current detection means, connected to said ignition plug via said secondary winding, for detecting an ion current generated due to combustion of said gas mixture by applying said high voltage to said at least one ignition plug; and
   restriction means, connected to said secondary winding of said ignition coil, for restricting a voltage generated in the secondary winding to a controlled voltage level when said primary winding is turned on to conduct;
   wherein said restriction means comprises a series circuit including a high tension diode and one of a resistor and a Zener diode respectively, said series circuit being connected across said secondary winding.

2. A combustion detection device for use in an internal combustion engine including an ignition coil, having a primary winding and a secondary winding, in which a high voltage for ignition is generated at an ignition high voltage generation end of said secondary winding when a current of said primary winding is cut off, and at least one ignition plug for discharging and igniting a gas mixture when said high voltage for ignition is applied to said at least one ignition plug, said combustion detection device comprising:
   ion current detection means, connected to said ignition plug via said secondary winding, for detecting an ion current generated due to combustion of said gas mixture by applying said high voltage to said at least one ignition plug; and
   restriction means, connected to said secondary winding of said ignition coil, for restricting a voltage generated in the secondary winding to a controlled voltage level when said primary winding is turned on to conduct;
   wherein said restriction means comprises a series circuit including a high tension diode and a Zener diode respectively, said series circuit being connected between one end of said secondary winding of said ignition coil and a coil power supply.

3. A combustion detection device for use in an internal combustion engine including an ignition coil, having a primary winding and a secondary winding, in which a high voltage for ignition is generated at an ignition high voltage generation end of said secondary winding when a current of said primary winding is cut off, and at least one ignition plug for discharging and igniting a gas mixture when said high voltage for ignition is applied to said at least one ignition plug, said combustion detection device comprising:
   ion current detection means, connected to said ignition plug via said secondary winding, for detecting an ion current generated due to combustion of said gas mixture by applying said high voltage to said at least one ignition plug; and
   restriction means, connected to said secondary winding of said ignition coil, for restricting a voltage generated in the secondary winding to a controlled voltage level when said primary winding is turned on to conduct;
   wherein said restriction means comprises a parallel circuit including a high tension diode and one of a resistor and a Zener diode respectively, said parallel circuit being connected between said ignition high voltage generation end of said secondary winding and said at least one ignition plug; and another high tension diode connected between the other end of said secondary winding and a connection point between said restriction means and said at least one ignition plug.

4. The combustion detection device as claimed in claim 1, wherein said internal combustion engine comprises a plurality of ignition plugs, and wherein said combustion detection device further comprises a distributor including a central electrode and a plurality of peripheral electrodes, wherein said central electrode is connected to said ignition high voltage generation end of said secondary winding, and wherein said peripheral electrodes are connected to respective ignition plugs corresponding to each cylinder in said internal combustion engine.

5. The combustion detection device as claimed in claim 2, wherein said internal combustion engine comprises a plurality of ignition plugs, and wherein said combustion detection device further comprises a distributor including a central electrode and a plurality of peripheral electrodes, wherein said central electrode is connected to said ignition high voltage generation end of said secondary winding, and wherein said peripheral electrodes are connected to respective ignition plugs corresponding to each cylinder in said internal combustion engine.

6. The combustion detection device as claimed in claim 3, wherein said internal combustion engine comprises a plurality of ignition plugs, and wherein said combustion detection device further comprises a distributor including a central electrode and a plurality of peripheral electrodes, wherein said central electrode is connected to said ignition high voltage generation end of said secondary winding, and wherein said peripheral electrodes are connected to respective ignition plugs corresponding to each cylinder in said internal combustion engine.

* * * * *